(12) United States Patent
Holtcamp et al.

(10) Patent No.: US 7,692,046 B2
(45) Date of Patent: Apr. 6, 2010

(54) HETEROGENEOUS ARYLALKYL OXIDATION PROMOTER

(75) Inventors: Matthew W. Holtcamp, Huffman, TX (US); Renuka N. Ganesh, Houston, TX (US); Tan-Jen Chen, Kingwood, TX (US); Jihad M. Dakka, Whitehouse Station, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 6 days.

(21) Appl. No.: 11/821,020

(22) Filed: Jun. 21, 2007

(65) Prior Publication Data

US 2008/0319234 A1    Dec. 25, 2008

(51) Int. Cl.
C07C 409/00    (2006.01)

(52) U.S. Cl. .................. 568/570; 502/103; 502/162; 502/167; 502/168; 502/172

(58) Field of Classification Search ............. 502/150, 502/155, 104, 100; 568/575, 574, 569, 571, 568/573, 567; 549/529, 530
See application file for complete search history.

(56) References Cited

U.S. PATENT DOCUMENTS

| | | | |
|---|---|---|---|
| 2,723,997 | A | 11/1955 | Reynolds |
| 3,010,915 | A | 11/1961 | Buell |
| 3,890,281 | A | 6/1975 | Angstadt |
| 4,870,217 | A | 9/1989 | Knifton |
| 5,147,527 | A | 9/1992 | Hettinger |
| 5,922,920 | A * | 7/1999 | Bond et al. ............ 568/342 |
| 6,825,387 | B2 | 11/2004 | Wilks |
| 6,906,189 | B2 * | 6/2005 | Busch et al. ........... 540/465 |
| 7,038,090 | B1 * | 5/2006 | Brandvold et al. ...... 568/575 |
| 7,361,792 | B2 * | 4/2008 | Brandvold et al. ...... 568/574 |
| 2004/0236152 | A1 | 11/2004 | Black et al. |

FOREIGN PATENT DOCUMENTS

| | | | |
|---|---|---|---|
| BR | 2004002790 | * | 6/2006 |
| CZ | 196648 | B1 | 7/1979 |
| EP | 0055311 | A1 | 7/1982 |
| EP | 0014802 | B1 | 3/1984 |
| EP | 0 578 194 | | 12/1994 |
| EP | 0951940 | A2 | 10/1999 |
| EP | 0729938 | B1 | 5/2001 |
| JP | 6-154619 | | 6/1994 |
| WO | WO 9736910 | * | 10/1997 |
| WO | 2006015826 | A1 | 2/2006 |
| WO | WO 2007/073916 | | 5/2007 |

OTHER PUBLICATIONS

Sorokin et al., Selective oxidation of aromatic compounds with dioxygen and peroxides catalyzed by phthalocyanine supported catalysts, Journal of Molecular Catalysis A: Chemical (2002), 182-183, 267-281.*
Boettcher et al., Aerobic oxidation of hydrocarbons catalyzed by electronegative iron salen complexes, Journal of Molecular Catalysis A: Chemical (1996), 113(1-2), 191-200.*
Cooke et al., Alkene epoxidation catalyzed by iron (III) and manganese(III) tetraarylporphyrins coordinatively bound to polymer and silica supports, Journal of the Chemical Society, Perkin Transactions 1: Organic and Bio-Organic Chemistry (1972-1999) (1994), (14), 1913-23.*
Evmenenko, Catalytic Activity of Metal Oxides of the Fourth Period in the Oxidation of Cumene, Kinet Katal V12 N.6 1437-41 (Nov.-Dec. 1971).
Navio, Selectivity and Mechanism of Cumene Liquid-Phase Oxidation in the Presence of Powdered Mixed Iron-Aluminum Oxides Prepared by Alkoxy Method, Applied Catalysis A: General 193/1-2 237-242 (2000228) (2000).
Srivastava, Kinetics of Liquid Phase Oxidation of Cumene with $Cr_2O_3$, $MnO_2$, and $Fe_2O_3$ Catalysts, J Catal V39 N.3 317-23 (Sep. 1975).

* cited by examiner

Primary Examiner—Sikarl A Witherspoon
Assistant Examiner—Chukwuma O Nwaonicha (57) ABSTRACT

A promoter can have utility in selective heterogeneous oxidation of arylalkyl hydrocarbons such as, for example, cyclohexyl benzene and/or sec-butyl benzene to form hydroperoxides. The promoter can include the product of contacting a solid support comprising a metal oxide surface and an iron compound. The solid support can include, for example, titanium dioxide and/or an iron oxide such as magnetite and can have magnetic susceptibility. A method for the oxidation of arylalkyl hydrocarbons to form hydroperoxides can include contacting 16 an arylalkyl hydrocarbon with oxygen in the presence of the promoter under catalytic oxidation conditions to form arylalkyl hydroperoxide, which can then be converted to phenol via cleavage 26. The method can include recovery 22 of the promoter from the arylalkyl hydroperoxide and can further include recycling the recovered promoter to the contacting 16. Where the solid support has magnetic susceptibility, the recovery 22 can include magnetic separation of the promoter.

33 Claims, 1 Drawing Sheet

FIGURE 1

HETEROGENEOUS ARYLALKYL OXIDATION PROMOTER

FIELD OF INVENTION

The invention relates to new oxidation promoters, and more particularly to heterogeneous promoters and processes for oxidizing arylalkyl hydrocarbons.

BACKGROUND

Organic hydroperoxides can be prepared by oxidizing arylalkyl hydrocarbons having a tertiary hydrogen with an oxygen containing gas. For example, the well known cumene hydroperoxide process employs air oxidation of cumene at a temperature of 80°-130° C. and elevated pressure with promoters such as sodium hydroxide or carbonate, followed by cleavage of the cumene hydroperoxide at 60°-100° C. with agitation under acidic conditions that can include a non-oxidizing acid such as sulfur dioxide gas. The resulting mixture of phenol, acetone and various byproducts is neutralized and separated to recover phenol and acetone in approximately equimolar proportions.

There are drawbacks to the cumene hydroperoxide process. Notably, the economics of the process for phenol production are tied to the market for acetone. The use of another arylalkyl hydrocarbon with an alkyl group other than isopropyl would yield a different ketone, however, air oxidation of such other arylalkyls can be problematic. The use of catalysts or other promoters to improve oxidation conversion rates and yields can complicate the downstream purification and/or cleavage reactions. The economics could be improved by the use of an oxidation promoter system that could be easily prepared, recovered and recycled.

SUMMARY OF THE INVENTION

This invention provides new oxidation systems and methods using a new class of promoters. A heterogeneous promoter for the oxidation of arylalkyl hydrocarbons to their respective hydroperoxides can have the advantageous properties of a selectivity of from about 80 percent and a conversion rate of from about 10 percent, while facilitating promoter recovery and recycle. Moreover, an embodiment of the promoter can include a solid support with natural magnetism, enabling magnetic separation of the promoter.

One embodiment of the invention provides a promoter for selective heterogeneous oxidation of arylalkyl hydrocarbons to form hydroperoxides. The system can include the product of contacting a solid support and an iron compound reactive therewith. The solid support can include a metal oxide surface. The iron compound can be in accordance with the formula:

$$(Fe^{+n}(X^1R^1R^2)_x(X^2R^3)_y X^3_z)M''_p \quad (I)$$

where n is the valence of Fe and has a value of 2 or 3; $R^1$, $R^2$ and $R^3$ are the same or different and are independently selected from hydrogen and hydrocarbyls and together any two of $R^1$, $R^2$ and $R^3$ may form a divalent hydrocarbyl; $X^1$ is nitrogen or phosphorus; $X^2$ is oxygen or sulfur; $X^3$ is halogen; M is a cation of valence n' where n' is from 1 to 3 (preferably 1, 2 or 3); and p, x, y and z are numerical values wherein z is 0 or 1, p is 0, 1 or 2, at least one of x and y is equal to or greater than 1, and $x+y+z=n+(n')(p)$ and $2 \leq (x+y+z) \leq 4$.

In an embodiment, the solid support includes iron oxide. In an embodiment, the solid support has magnetic susceptibility. In an embodiment, the solid support includes magnetite. In another embodiment, the solid support includes hematite.

In another embodiment, the solid support includes titanium dioxide.

In an embodiment, $R^1$, $R^2$ and $R^3$ are selected from alkyl groups having from 1 to 30 carbon atoms and aryl and aralkyl groups having from 6 to 30 carbon atoms. In another embodiment, M is selected from the group consisting of alkali metal cations, ammonium and phosphonium.

In another embodiment a slurry can include the reaction product on the support dispersed in a carrier liquid.

Another embodiment of the invention provides a method for oxidation of arylalkyl hydrocarbons to form hydroperoxides. The method can include: contacting an arylalkyl hydrocarbon with oxygen in the presence of a promoter under catalytic oxidation conditions to form arylalkyl hydroperoxide. The promoter can include the product of contacting: a solid support including a metal oxide surface and the iron compound discussed above.

An embodiment of the method can include recovering the promoter from the arylalkyl hydroperoxide. In an embodiment, the recovery can include filtration or centrifugation. In another embodiment, the solid support has magnetic susceptibility and the recovery can include magnetic separation. Another embodiment can include recycling the recovered promoter to the arylalkyl hydrocarbon-oxygen contacting.

An embodiment can further include slurrying the promoter in a carrier liquid for the contacting.

In various embodiments, the arylalkyl hydrocarbon can include cumene, cyclohexyl benzene, sec-butyl benzene, or the like.

DETAILED DESCRIPTION

For purposes of this invention and the claims thereto the term "promoter" refers to a complex used to modify the rate of a chemical reaction. The promoter can include a catalyst or catalyst system in one embodiment, and a free radical catalyst in another embodiment.

"Alkyl" refers to a paraffinic hydrocarbon group which can be derived from an alkane by dropping one or more hydrogens from the alkane formula, such as, for example, a methyl group ($CH_3$), or an ethyl group ($CH_3CH_2$), etc. "Aryl" refers to a hydrocarbon group that forms a ring structure characteristic of aromatic compounds such as, for example, benzene, naphthalene, phenanthrene, anthracene, etc., and typically possesses alternate double bonding ("unsaturation") within its structure. An aryl group is thus a group derived from an aromatic compound by dropping one or more hydrogens from the aromatic compound formula such as, for example, phenyl, or $C_6H_5$.

The term "arylalkyl" refers to a radical containing both aliphatic and aromatic structures, the radical being at either an alkyl position or an aryl position. The term thus includes both substances with radicals at alkyl positions and substances with radicals at aryl positions.

A "hydroperoxide" is a monosubstitution product having the skeleton ROOH, in which R is any organyl group.

An "initiator" is a substance or molecule, other than a reactant, that induces a reaction.

A "hydrocarbyl" is a univalent group formed by removing a hydrogen atom from a hydrocarbon.

An "aralkyl" is a radical in which an aryl group is substituted for an alkyl H atom.

The promoter can include either a magnetic or magnetizable metal and the term "magnetic" is to be construed as including both classes. Thus, the expression "magnetic" includes both promoters which are inherently magnetic and promoters which are capable of being magnetized, at least momentarily, during passage through a magnetic field.

As used herein, the new numbering scheme for the Periodic Table Groups are used as published in CHEMICAL AND ENGINEERING NEWS, 63(5), 27 (1985).

The promoter in one embodiment can include the product of contacting a solid support including a metal oxide surface and an iron compound. The promoter can further include unreacted reagents, and can include mixed phases, wherein the iron compound exists in a phase distinct from the metal oxide and the solid support.

A suitable metal oxide can include a compound of oxygen and a metal, which can be selected from, but is not limited to, the group including alkali metals, alkaline earth metals, rare earth metals, transition metals and main group metals. Specific representative examples include, but are not limited to, oxides of iron, titanium, manganese, cobalt, chromium, vanadium, molybdenum, copper, nickel, zinc, gallium, aluminum, indium, magnesium, and the like or a combination thereof. In one embodiment, the metal oxide can provide a reactive site such as hydroxyl or an abstractable proton to react with, associate with or otherwise bind an iron compound as described herein to the metal oxide surface wherein the bound iron compound can function as an active or activatable oxidation promoter for selective oxidation of an arylalkyl hydrocarbon to the hydroperoxide.

Metal oxides can be simple oxides, complex oxides, anhydrous states of the foregoing oxides, and the like or a combination thereof. Simple metal oxides are compounds with formulations such as:

$$(M1)_a^{m1+}O_z$$

where M1 is a metal, a is the moles of the M1 metal in the metal oxide and is defined to be equal to 1, m1 is the valence of M1 and z is the mole ratio of O to M1.

In the anhydrous state, simple metal oxides have formulations such as:

$$(M1)_a^{m1+}H_dO_z,$$

where d is the mole ratio of hydrogen to M1, and M1, a, m1, O, and z are as defined above.

Complex metal oxides have formulations such as:

$$(M1)_a^{m1+}(M2)_b^{m2+}O_z,$$

$$(M1)_a^{m1+}(M2)_b^{m2+}(M3)_c^{m3+}O_z$$

and the like, and their respective anhydrous states can have formulations such as:

$$(M1)_a^{m1+}(M2)_b^{m2+}H_dO_z,$$

$$(M1)_a^{m1+}(M2)_b^{m2+}(M3)_c^{m3+}H_dO_z$$

and the like or a combination thereof, where M1, a, d, m1, O, and z are as defined above, M2 and M3 are metals, b and c are the respective mole ratios of the M2 and M3 metals to M1, m2 and m3 are the respective valences of M2 and M3.

Examples of suitable metal oxides include, but are not limited to, iron oxides, titanium oxides, magnesium oxides, aluminum oxides and zirconium oxides. Preferably, the solid support includes an iron oxide such as magnetite or hematite, titanium dioxide such as rutile, or the like, or a combination thereof. Metals useful for M1, M2 and or M3 include, independently, Fe, Ti, Mg, Al and Zr.

In the oxidation of, for example, sec-butyl benzene or another arylalkyl hydrocarbon to its respective hydroperoxide, a promoter formed by contacting the solid support with an iron compound wherein the solid support includes magnetite can have the advantageous properties of a selectivity of about 80%, a conversion rate of about 10% and, strikingly, a solid support with natural magnetism which makes it easily recyclable.

In the oxidation of, for example, sec-butyl benzene, cyclohexyl benzene or another arylalkyl hydrocarbon to its respective hydroperoxide, a promoter formed by contacting the solid support with an iron compound wherein the solid support includes a titanium oxide can advantageously obtain selectivities of about 80% to 90% and conversions of about 10% to 20%, depending on promoter loading, structure and solid support surface area.

The amount of metal oxide on the solid support surface can range widely, depending on, for example, the surface area of the solid support, the desired loading of the iron-compound reaction product, the stoichiometry of the reaction with the iron compound, the reactivity and conditions for oxidation of the arylalkyl hydrocarbon, etc. The solid support can have a surface area in various embodiments from 0.01 to 600 m$^2$/g, preferably from 1 to 500 m$^2$/g, and especially from 2 to 300 m$^2$/g. Loadings of the iron compound on the solid support can range, in various embodiments, from 0.01 weight percent to 20 weight percent, preferably from 0.1 weight percent to 10 weight percent, and especially 0.3 weight percent to 3 weight percent, based on the total weight of the iron compound-solid support contact product. Where there are no losses of solid support/metal oxide other than formation of the contact product at the surface, the iron compound loading can be taken as the quotient of the weight increase of the solid support divided by the final or total weight of the iron-compound-solid support contact product.

In one embodiment, the solid support comprises homogenous metal oxide, e.g. pure metal oxide or a naturally occurring metal oxide mineral such as rutile, hematite, magnetite, bauxite, or the like. In another embodiment, the solid support can comprise a coating or exterior surface or layer of metal oxide over an inert core. The coating can be formed by depositing a layer of the metal oxide over core particles, or it can be formed by surface oxidation or hydration of a metal core, e.g. oxidation of aluminum or iron particles to the corresponding oxide.

Generally, the amount of metal oxide will be in the range from about 0.1 to about 100 weight percent and preferably from about 1 to about 99.9 weight percent based on the total weight of the solid support and metal oxide.

A solid support can further include one or more optional materials such as a phosphate, silicate, germinate, carbonate and the like, or a combination thereof, of one or more metals, in addition to the metal(s) of the metal oxide surface. Examples of optional materials can include, but are not limited to, lithium zirconate, hydroxyapatite, a metal, metal oxide which is different than the surface metal oxide, or any other inert core material, and the like or a combination thereof.

A suitable iron compound can, for example, have the formula $(Fe^{+n}(X^1R^1R^2)_x(X^2R^3)_yX^3_z)M''_p$ wherein n is the valence of Fe and has a value of 2 or 3; R$^1$, R$^2$ and R$^3$ are the same or different and are independently selected from hydrogen and hydrocarbyls and together any two of $R^1$, $R^2$ and $R^3$ may form a divalent hydrocarbyl; $X^1$ is nitrogen or phosphorus; $X^2$ is oxygen or sulfur; $X^3$ is a halogen; M is a cation of valence n' where n' is from 1 to 3; and p, x, y and z are numerical values wherein z is 0 or 1, p is 0, 1 or 2, at least one of x and y is equal to or greater than 1, and $x+y+z=n+(n')(p)$ and $2 \leq (x+y+z) \leq 4$. In many instances, suitable iron compounds can include iron indolyls or amides such as iron(III) triphenylamide.

Suitable examples for $R^1$, $R^2$ and $R^3$ can include, but are not limited to, alkyl groups having from 1 to 30 carbon atoms, aryl and aralkyl groups having from 6 to 30 carbon atoms and the like or a combination thereof. Preferably, an alkyl group $R^1$, $R^2$ or $R^3$ can, individually, include from about 1 to about 10 carbon atoms. Preferably, an aralkyl group $R^1$, $R^2$ or $R^3$ can, individually, include from about 7 to about 10 carbon atoms. Specific non-limiting representative examples of $R^1$, $R^2$ and/or $R^3$ include methyl, ethyl, propyl, butyl, phenyl, tolyl, xylyl, and the like. Specific non-limiting representative examples of $-X^1R^1R^2$, where $R^1$ and $R^2$ together form a divalent hydrocarbyl bridge, include pyridyl, indolyl, 2,3-dimethylindolyl and the like.

Suitable examples of M can include cations of valence n' where n' is from 1 to 3. There are various cations with such valences which can be used to form an electrically neutral material. Preferably, M is selected from the group consisting of alkali metal cations, ammonium and phosphonium. Representative non-limiting examples include lithium, potassium, sodium and the like.

Suitable examples of $X^3$ include chloride, bromide, fluoride, iodide, etc., preferably chloride or bromide.

Specific representative non-limiting examples of the iron compound include: iron(III) trimethysilylamide, iron diphenylamide bromide, potassium iron 2,3-dimethylindolyl bromide, iron(III) 5,6-dimethylindolyl, iron ethoxide, potassium iron(III) tetrakisindolyl and the like.

A promoter embodiment can be prepared by contacting the metal oxide surface of the solid support with a solution or dispersion of the iron compound. The amount of iron compound to react can depend on, inter alia, the amount of metal oxide surface on the solid support. In general, a stoichiometric equivalent or excess of the iron compound can be employed to obtain complete saturation of the metal oxide surface, i.e., essentially complete reaction of the reactive sites on the metal oxide surface to equilibrium, but in an embodiment a substoichiometric amount of the iron compound can be used to control the saturation level, e.g. a saturation of from 0.1 to 90 percent.

A slurry can be obtained by dispersing the support in a carrier liquid in a flask or other suitable vessel at a ratio of, for example, from about 2 to about 10 mL of liquid carrier per gram of solid support in one embodiment. The dispersion can then be swirled, stirred or otherwise agitated to enhance mixing. Liquid carriers for preparation of the promoter can include a suitable solvent for the iron compound, such as, for example, toluene, tetrahydrofuran, cumene and the like or a combination thereof. The metal oxide on the surface of the solid support is allowed to react with the iron compound at a suitable temperature for a suitable period of time to complete any reaction or association between the metal oxide and the iron compound. The temperature is conveniently the boiling point or just below the boiling point of the solution at atmospheric pressure, but can be any temperature such as from about 25° C. to about 200° C., preferably from about 80° C. to about 180° C. The pressure utilized for the promoter preparation can be atmospheric or superatmospheric and will generally range from about 100 kPa to about 7.0 MPa and will preferably range from about 100 kPa to about 3.5 MPa. The time of reaction can be from 5 minutes to 2 days, e.g. overnight.

Suitable arylalkyl hydrocarbons which can be oxidized with the promoter according to one embodiment can have the formula:

where Ar is an aromatic hydrocarbon group having a valence of x, (in some embodiments, x may be 1, 2, 3, 4, 5, 6, 7, or 8) and T and Q can be the same or different from each other and can be hydrogens or alkyls. The arylalkyl hydrocarbon can have at least one alpha hydrogen in the molecule. The arylalkyl hydrocarbon can have a hydrogen bonded to a primary, secondary or tertiary carbon atom.

Suitable alkyl groups can include any group of atoms derived from an alkane by the removal of one hydrogen atom including, for example, methyl, ethyl, propyl, butyl and the like.

Examples of suitable arylalkyl hydrocarbons can include, but are not limited to, diisopropyl benzenes such as cumene, cymene, m-diisopropyl benzene and p-diisopropyl benzene, triisopropyl benzenes such as 1,3,5-triisopropyl benzene, ethyl benzene, sec-butyl benzene, sec-butylethyl benzene, isopropyl naphthalenes, diisopropyl naphthalenes such as 2,6-diisopropyl naphthalene, isopropyl biphenyls, diisopropyl biphenyls such as 4,4'-diisopropylbiphenyl, cyclohexyl benzene, and the like or combinations thereof.

The oxidation reaction can be carried out by contacting the arylalkyl hydrocarbon with oxygen in the presence of the promoter under catalytic oxidation conditions. The oxidation reaction can be carried out, for example, in a batch or continuous reactor that is capable of withstanding the oxidizing conditions.

The amount of promoter utilized can be any catalytically effective amount. Generally, this amount can be in the range from about 0.001 to about 10 weight percent and preferably from about 0.01 to about 5 weight percent based on the weight of an arylalkyl hydrocarbon feedstock, which can be obtained from commercial sources. In the case where the promoter is employed in a fixed bed and the hydrocarbon feedstock is passed over the promoter, the liquid hourly space velocity (LHSV) based on the hydrocarbon feedstock can be in the range from about 0.01 to about 40 per hour and preferably from about 0.1 to about 25 per hour.

Air, oxygen, oxygen-enriched air, as well as other mixtures of gases with oxygen, can be utilized as the source of oxygen. Any suitable amount of oxygen can be employed. Preferably, oxygen can be employed in an amount effective to substantially convert the arylalkyl hydrocarbon. The amount of oxygen employed can be expressed in terms of the mole ratio of oxygen to that of the arylalkyl hydrocarbon that is to be oxidized. Generally, this ratio can be in the range from about 0.005:1 to about 20:1 or higher and preferably in the range of about 0.01:1 to about 2:1.

The oxygen can be introduced into an oxidation zone in any manner that will result in oxygen contacting the feedstock to be oxidized. For example, the reaction mixture can be stirred under an oxygen atmosphere at atmospheric pressure or above, or air or other oxygen-containing gas can be bubbled through the reaction mixture. Air can be introduced, e.g., via a blower and discharged to a vent. In a continuous process, the reagents can be passed through an oxidation zone including a promoter embodiment, e.g. in slurry form, and oxidation product effluent then treated to remove promoter and/or sent to a further processing stage such as cleavage, purification, and the like or a combination thereof.

The pressure utilized during the oxidation reaction can be atmospheric or superatmospheric and will generally range from about 100 kPa to about 7.0 MPa and will preferably range from about 100 kPa to about 3.5 MPa. The oxidation reaction temperature can be in the range of from about 25° C. to about 200° C., preferably from about 80° C. to about 180° C. Lower temperatures can result in higher selectivity to hydroperoxides.

The contact time of the reagents and the promoter can depend upon the temperature employed and the degree of conversion that is desired. At prolonged times, the yield of hydroperoxides can increase up to a point and can then decline because of decomposition of the hydroperoxides. Generally, in a static reaction system, the oxidation reaction can be conducted for a time in the range of from about 5 minutes to 2 days. However longer or shorter times are possible.

For example, oxidation of sec-butyl benzene to the corresponding hydroperoxide can be accomplished by introducing oxygen into a liquid phase containing the sec-butyl benzene in the presence of a promoter embodiment. The reaction can be performed in the absence of a promoter but is slow, of the order of less than 1% per hour at about 700 kPa. Improvement in the reaction rate, selectivity and conversion rates can be achieved by performing the oxidation in the presence of a promoter embodiment.

Suitable conditions for sec-butyl benzene oxidation, for example, include a temperature from about 70° C. to about 200° C., such as about 90° C. to about 130° C., and a pressure of from about 50 to 1000 kPa. A basic buffering agent can be added to react with acidic by-products that can form during the oxidation. In addition, an aqueous phase can be introduced, which can help dissolve basic compounds, such as sodium carbonate. The per-pass conversion during oxidation can be kept low, below 50% in one embodiment, to inhibit the formation of byproducts. The oxidation reaction can, for example, be conducted in a catalytic distillation unit and the sec-butyl benzene hydroperoxide produced can be concentrated by distilling off unreacted sec-butyl benzene.

During the oxidation, a portion of a previous reaction mixture or product can be utilized as an ingredient in the charge of a fresh feedstock since this can lessen or eliminate an induction period that might otherwise occur. Induction periods can also be lessened or eliminated by the addition of a small amount of a hydroperoxide other than the hydroperoxide product expected. In this context, the hydroperoxide can be an initiator. Hydroperoxides that are suitable initiators can be those which decompose under the reaction conditions quickly enough to reduce the induction periods. Examples of suitable initiators include, but are not limited to, cumene hydroperoxide and cyclohexyl benzene hydroperoxide. Generally, hydroperoxide initiators can be effective in amounts in the range of from about 0.5 to about 1.5 weight percent of the fresh feedstock, based on the weight of the fresh feedstock at the initiation of the oxidations reaction. The promoter can be used either with or without an initiator.

Following the oxidation reaction, the promoter can be removed from the hydroperoxide via separation techniques such as filtration, centrifugation, magnetic separation and the like or a combination thereof. For example, the promoter can settle under gravity and liquid reaction products can then be decanted or filtered from the solid promoter. Centrifugation can be used to increase the settling rate of, for example, finely divided solid promoter particulates which are suspended in a reaction medium. In one embodiment, the solid support can have magnetic susceptibility and magnetic separation can be convenient. EP 014 802 B2 to Imperial Chemical Industries, for example, discloses a process wherein catalyst particles in a liquid reaction mixture in a reactor are magnetically flocculated and allowed to settle to produce a supernatant liquid phase which is withdrawn from the reactor, leaving the catalyst particles in the reactor. For another example, U.S. Pat. No. 3,010,915 to Buell, et al., discloses a process for recycling magnetically separated nickel on kieselguhr, or diatomite, catalyst for further reactions. The recovered promoter can be recycled to the oxidation reaction zone in one embodiment.

A recovery system can be supplemented with promoter makeup, e.g., in a continuous process, whereby fresh promoter is added to the recovery system to aid in maintaining an appropriate promoter concentration during oxidation. Promoter makeup can be useful, for example, to offset promoter losses due to incomplete recovery or to increase the promoter concentration due to changed process conditions; similarly, recovered promoter can be removed from the process to lower the promoter concentration. Further, although as shown in Table 2 the promoter can retain advantageous yield, conversion and selectivity properties even after being recycled, a portion of the recovered promoter can nevertheless be withdrawn from the system and replaced with a fresh portion to avoid the buildup of catalyst which has become inert or less active in an embodiment.

Hydroperoxides can be converted to other compounds via known cleavage reactions. For example, after oxidizing sec-butyl benzene, cleaving the resulting hydroperoxide can produce phenol and methyl ethyl ketone. The cleavage reaction can be effected by contacting the sec-butyl benzene hydroperoxide with a catalyst in a liquid phase at a temperature of from about 20° C. to about 150° C., such as about 40° C. to about 120° C., a pressure of from about 50 to about 2500 kPa, such as from about 100 to about 1000 kPa and an LHSV based on the hydroperoxide of from about 0.1 to about 100 per hour, preferably from about 1 to about 50 per hour. The sec-butyl benzene hydroperoxide can be diluted in an organic solvent inert to the cleavage reaction, such as methyl ethyl ketone, phenol or sec-butyl benzene, to assist in heat removal. The cleavage reaction can be conveniently conducted in a catalytic distillation unit. The catalyst employed during cleavage can be a homogeneous catalyst or a heterogeneous catalyst. Suitable homogeneous cleavage catalysts can include sulfuric acid, perchloric acid, phosphoric acid, hydrochloric acid and p-toluenesulfonic acid. Ferric chloride, boron trifluoride, sulfur dioxide and sulfur trioxide can also be effective homogeneous cleavage catalysts. A preferred homogeneous cleavage catalyst is sulfuric acid. A suitable heterogeneous catalyst for use in the cleavage of sec-butyl benzene hydroperoxide can include a smectite clay, such as an acidic montmorillonite silica-alumina clay, as described in U.S. Pat. No. 4,870,217 to Knifton. Cleavage products such as phenol and ketones can be separated, washed and further treated. U.S. Pat. No. 6,825,387 to Wilks, et al., for example, discloses removing salts from washed cleavage products from the reaction of cumene hydroperoxide with an acid catalyst.

Figure 1:
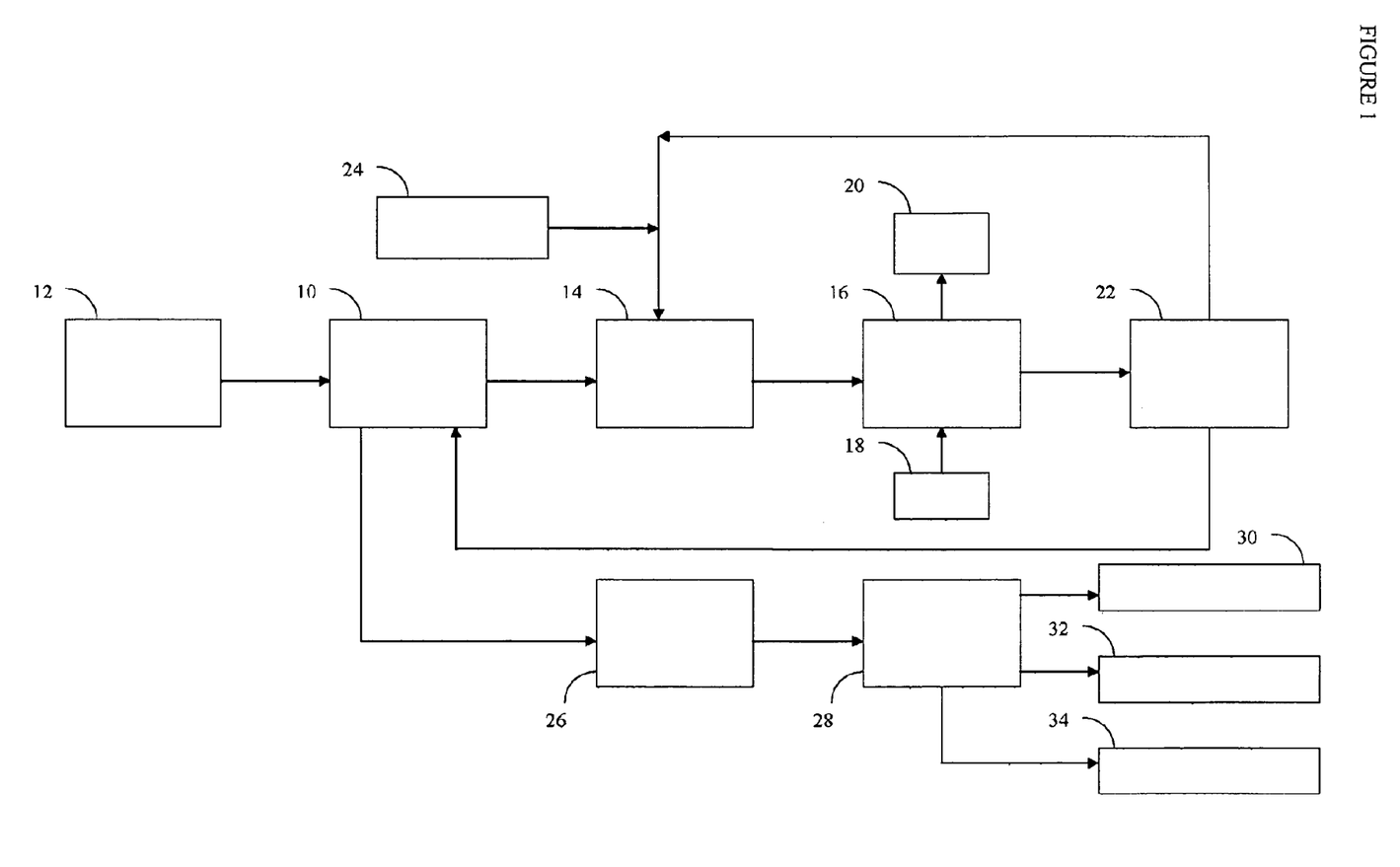
FIG. 1 is a schematic flow diagram of an arylalkyl hydrocarbon oxidation process according to an embodiment of the invention.

FIG. 1 illustrates a process for producing peroxide and, subsequently, phenol and ketones from an arylalkyl hydrocarbon. As shown in FIG. 1, a feed concentration/peroxide recovery zone 10 can be supplied with, for example, sec-butyl benzene, from an arylalkyl hydrocarbon feed source 12. In a slurrying zone 14, the arylalkyl hydrocarbon can be slurried with the promoter, which can include a magnetite-based solid support, and any diluent. In an oxidation zone 16 the slurried arylalkyl hydrocarbon can be contacted with oxygen in the presence of the promoter under catalytic oxidation conditions to form oxidation products such as arylalkyl hydroperoxide. An air source 18 can supply the oxygen to the oxidation zone 16 and spent air from the oxidation zone 16 can be exhausted to a spent air receiving zone 20.

The promoter can be recovered from a promoter separation zone 22, e.g., magnetically, from oxidation products and recycled to the slurrying zone 14. A promoter makeup source 24 can supplement the recycled promoter to account for promoter loss during slurrying 14, oxidation 16 or separation 22. The feed concentration/peroxide recovery zone 10 can divert a portion of hydroperoxide from the oxidation products to a cleavage zone 26. Another portion of the hydroperoxide, however, can be utilized as an ingredient in the charge to the slurrying zone 14, e.g., mixed in a combined stream with the feed sec-butyl benzene, to lessen an induction period. Further, the feed concentration/peroxide recovery zone 10 can withdraw unreacted sec-butyl benzene from oxidation products and reroute the unreacted sec-butyl benzene to the slurrying zone 14. A product mixture stream from the cleavage zone 26 can be separated in a cleavage product separation zone 28, and the separated cleavage products discharged to phenol 30, ketones 32 and other byproducts 34 receiving zones.

In another embodiment this invention relates to:

1. A promoter for selective heterogeneous oxidation of arylalkyl hydrocarbons to form hydroperoxides, comprising the product of contacting:
    a solid support comprising a metal oxide surface; and
    an iron compound according to the formula $(Fe^{+n}(X^1R^1R^2)_x(X^2R^3)_yX^3_z)M^{n'}_p;$ wherein n is the valence of Fe and has a value of 2 or 3; $R^1$, $R^2$ and $R^3$ are the same or different and are independently selected from hydrogen and hydrocarbyls and together any two of $R^1$, $R^2$ and $R^3$ may form a divalent hydrocarbyl; $X^1$ is nitrogen or phosphorus; $X^2$ is oxygen or sulfur; $X^3$ is halogen; M is a cation of valence n' where n' is from 1 to 3 (preferably 1, 2 or 3); and p, x, y and z are numerical values wherein z is 0 or 1, p is 0, 1 or 2, at least one of x and y is equal to or greater than 1, and $x+y+z=n+(n')(p)$ and $2 \leq (x+y+z) \leq 4$.

2. The promoter of paragraph 1, wherein the solid support comprises iron oxide.
3. The promoter of paragraph 1 or 2, wherein the solid support has magnetic susceptibility.
4. The promoter of any of the above paragraphs 1 to 3, wherein the solid support comprises magnetite.
5. The promoter of any of the above paragraphs 1 to 4, wherein the solid support comprises hematite.
6. The promoter any of the above paragraphs 1 to 5, wherein the solid support comprises titanium dioxide.
7. The promoter of any of the above paragraphs 1 to 6, wherein $R^1$, $R^2$ and $R^3$ are selected from alkyl groups having from 1 to 30 carbon atoms and aryl and aralkyl groups having from 6 to 30 carbon atoms.
8. The promoter of any of the above paragraphs 1 to 7, wherein M is selected from the group consisting of alkali metal cations, ammonium and phosphonium.
9. The promoter of any of the above paragraphs 1 to 8 further comprising a slurry of the contact product on the support dispersed in a carrier liquid.
10. A method for oxidation of arylalkyl hydrocarbons to form hydroperoxides, comprising:
    contacting an arylalkyl hydrocarbon with oxygen in the presence of a promoter under catalytic oxidation conditions to form arylalkyl hydroperoxide;

wherein the promoter comprises the product of contacting:
    a solid support comprising a metal oxide surface; and $(Fe^{+n}(X^1R^1R^2)_x(X^2R^3)_yX^3_z)M^{n'}_p;$ wherein n is the valence of Fe and has a value of 2 or 3; $R^1$, $R^2$ and $R^3$ are the same or different and are independently selected from hydrogen and hydrocarbyls and together any two of $R^1$, $R^2$ and $R^3$ may form a divalent hydrocarbyl; $X^1$ is nitrogen or phosphorus; $X^2$ is oxygen or sulfur; $X^3$ is halogen; M is a cation of valence n' where n' is from 1 to 3; and p, x, y and z are numerical values wherein z is 0 or 1, p is 0, 1 or 2, at least one of x and y is equal to or greater than 1, and $x+y+z=n+(n')(p)$ and $2 \leq (x+y+z) \leq 4$.

11. The method of paragraph 10, wherein $R^1$, $R^2$ and $R^3$ are selected from alkyl groups having from 1 to 30 carbon atoms and aryl and aralkyl groups having from 6 to 30 carbon atoms.
12. The method of paragraph 10 or 11, wherein M is selected from the group consisting of alkali metal cations, ammonium and phosphonium.
13. The method of any of the above paragraphs 10 to 12, further comprising recovering the promoter from the arylalkyl hydroperoxide.
14. The method of any of the above paragraphs 10 to 13 wherein the recovery comprises filtration or centrifugation.
15. The method of any of the above paragraphs 10 to 14 wherein the solid support has magnetic susceptibility and the recovery comprises magnetic separation.
16. The method of any of the above paragraphs 10 to 15, further comprising recycling the recovered promoter to the contacting.
17. The method of any of the above paragraphs 10 to 16, further comprising slurrying the promoter in a carrier liquid for the contacting.
18. The method of any of the above paragraphs 10 to 17, wherein the arylalkyl hydrocarbon comprises cumene.
19. The method of any of the above paragraphs 10 to 17, wherein the arylalkyl hydrocarbon comprises cyclohexyl benzene.
20. The method of any of the above paragraphs 10 to 17, wherein the arylalkyl hydrocarbon comprises sec-butyl benzene.
21. The method of any of the above paragraphs 10 to 20, wherein the solid support comprises iron oxide.
23. The method of any of the above paragraphs 10 to 20, wherein the solid support comprises magnetite.
24. The method of any of the above paragraphs 10 to 20, wherein the solid support comprises hematite.
25. The method of any of the above paragraphs 10 to 20, wherein the solid support comprises titanium dioxide.

EXAMPLES

Terms used in the following examples include SBB (sec-butyl benzene), CHB (cyclohexyl benzene), and ph is phenyl. "Yield" in reference to oxidation refers to the yield of the alkyl benzene hydroperoxide.

The promoters used in the following examples have the general formulae:

$$M_nFe(NR_2)_xX_y \quad (A)$$

$$M_nFe(OR)_xX_y \quad (B)$$

where M is a Group 1 or 2 metal cation (preferably potassium) and may or may not be solvated; x+y=2, 3 or 4; n=0 when x+y=2; n=0, 1 or 2 when x+y=3; and n=1 or 2 when x+y=4, NR$_2$ is diphenylamino or 2,3-dimethylindolyl, OR is ethoxy, and X is Br. For preparation of the promoters, the solvents (from Sigma-Aldrich) were dried with previously calcined (300° C.) alumina beads. Magnetite, TiO$_2$ and Fe(III) ethoxide (from Alfa Aesar) were purged overnight under nitrogen. Diphenylamine, 2,3-dimethylindole (from Sigma-Aldrich) and Fe(III) bromide (from Strem Chemicals), were used as purchased.

Several promoter examples were prepared with either (Fe(NPh$_2$)$_2$Br)$_n$ or (KFe(2,3-Me$_2$indolyl)$_x$Br$_y$)$_n$, where x+y=4 and n is 1, 2 (dimeric) or more. To synthesize the (Fe(NPh$_2$)$_2$Br)$_n$, initially 41.5 grams of diphenylamine were dissolved into 350 mL of tetrahydrofuran. While this mixture was stirred with a spatula, 9.94 grams of potassium hydride were added in small portions. When hydrogen evolution ceased, 24.3 grams of iron(III) bromide were added in portions. The resulting slurry was stirred overnight then filtered. The filtrate was dried under vacuum overnight. Pentane (300 mL) was added to slurry the product. The product, a dark blue powder, was filtered and dried, yielding 32.5 grams of solid.

To synthesize the (KFe(2,3-Me$_2$indolyl)$_x$Br$_y$)$_n$ species, 20.1 grams of 2,3-dimethylindole were initially dissolved into 300 mL of tetrahydrofuran. Potassium hydride (5.6 g) was then added via spatula slowly over several hours. When hydrogen evolution ceased, 13.7 grams of iron(III) bromide were added slowly in small portions. The resulting slurry was stirred overnight. The slurry was filtered, and the filtrate was dried under vacuum overnight. Toluene (250 mL) was added to the residue and the resulting slurry was stirred for several days. The toluene slurry was filtered, and approximately 20 grams of a dark blue-black powder product were obtained.

For each oxidation reaction, a 250-mL round bottom flask fitted with a condenser, stirrer and an air sparger, was charged with an alkyl benzene and a promoter. The flask was heated using a temperature-controlled heating mantle. The reaction temperature was maintained at 110° C. or 115° C. The reaction pressure was atmospheric. The air flow rate was maintained at 220 mL per minute. Every 45 minutes and after six hours, a small aliquot of the reaction mixture was removed from the flask and analyzed by gas chromatography (GC), high performance liquid chromatography (HPLC) and titration.

Promoter Example 1

(Fe(NPh$_2$)$_2$Br)$_n$ (1.0 g) was dissolved in 20 mL toluene in a flask. Fe$_3$O$_4$ (10.0 g) was added to this solution, and the flask was swirled to form a slurry. The slurry was maintained at 60°-150° C. overnight. The slurry was then allowed to cool to room temperature and a magnet was used to separate a black solid from the black solution. The solid washed twice and dried under vacuum overnight to yield 10.12 g.

Promoter Example 2

(Fe(NPh$_2$)$_2$Br)$_n$ (2.2 g) was combined in 20 mL of cumene with 3.8 g of hematite and maintained at 125° C. overnight. The resulting Fe(NPh$_2$)$_2$Br$_n$-hematite slurry was filtered, rinsed with several 10-mL portions of cumene and dried.

Promoter Example 3

(KFe(2,3-Me$_2$indolyl)$_x$Br$_y$)$_n$ (1.2 g) was combined with 10.0 g of magnetite in 45 mL of cumene and maintained at 100° C. overnight. The resulting slurry was allowed to cool to room temperature, and a magnet was used to separate the black powdery solid promoter from the solution. The supported (KFe(2,3-Me$_2$indolyl)$_x$Br$_y$)-magnetite material was rinsed with several 10-mL portions of cumene and dried.

Promoter Example 4

Fe(III) ethoxide (0.5 g) was mixed with 30 mL of tetrahydrofuran. Magnetite (5.0 g) was added to the mixture, and the resulting slurry was maintained at 60° C. overnight. The slurry was filtered, twice rinsed with 10-mL portions of tetrahydrofuran and the recovered Fe(OEt)$_n$-magnetite was dried.

Oxidation Examples 5-9

The yield, conversion and selectivity of the alkyl benzene oxidation reactions with magnetite (Example 5, comparative) and selected magnetite- and hematite-supported promoters are provided in Table 1 below.

TABLE 1

| | Oxidation with Magnetite- and Hematite-Supported Promoters | | | | | | |
|---|---|---|---|---|---|---|---|
| | Alkyl Benzene | | Promoter | | | Conversion | Selectivity |
| Example | Type | Qty. (g) | Type | Qty. (g) | Yield (%) | (%) | (%) |
| 5 | CHB | 40 | Magnetite | 0.4 | 8.78 | 10.24 | 85.70 |
| 6 | CHB | 40 | P. Ex. 2 | 0.1 | 14.20 | 17.40 | 81.58 |
| 7 | CHB | 40 | P. Ex. 3 | 0.4 | 13.17 | 16.44 | 80.11 |
| 8 | CHB | 40 | P. Ex. 4 | 0.4 | 16.28 | 19.00 | 85.72 |
| 9 | SBB | 120 | P. Ex. 4 | 0.2 | 6.68 | 8.00 | 83.50 |

Promoter Example 10

The preparation of Promoter 10 was the same as that of Promoter Example 3, except that 2.0 g (rather than 1.2 g) of KFe(2,3-Me$_2$indolyl)$_x$Br$_y$)$_n$ were used.

Oxidation Examples 11 and 12

Promoter Example 10 was used in Oxidation Example 11 to oxidize cyclohexylbenzene. The "used" promoter recovered following Oxidation Example 11 was then recovered via a magnetic stir bar and reused as the promoter for Oxidation Example 12. The yield, conversion and selectivity of the alkyl benzene oxidation reactions with the fresh and the recycled Promoter Example 10 are provided in Table 2 below.

TABLE 2

Oxidation with Fresh and Recycled Magnetite-Supported Promoter

| Example | Alkyl Benzene Type | Qty. (g) | Promoter Type | Qty. (g) | Yield (%) | Conversion (%) | Selectivity (%) |
|---|---|---|---|---|---|---|---|
| 11 | CHB | 40 | P. Ex. 10 | 0.40 | 9.7 | 11.0 | 88.2 |
| 12 | CHB | 40 | P. Ex. 10 (recycled) | 0.37 | 10.1 | 11.4 | 88.2 |

Examples 1-12 demonstrate the preparation and effect of the promoters prepared on iron supports in the oxidation of alkyl benzenes. In the oxidation of sec-butyl benzene or cyclohexyl benzene, a promoter prepared on magnetite can have a selectivity of 80% or more and a conversion to the hydroperoxide of 15% or more. Moreover, the advantageous characteristics of a promoter can be retained when the promoter is recycled.

Promoter Example 13

$Fe(N(C_6H_5)_2Br)_n$ (1.0 g) was dissolved in 30 mL toluene in a flask. $TiO_2$ (rutile) (10.0 g) was added to this solution, and the flask was swirled to form a slurry. The slurry was maintained at 100° C. overnight. The slurry was then allowed to cool to room temperature, filtered, washed with toluene, and dried under vacuum overnight to yield 10 g of supported promoter $Fe(N(C_6H_5)_2Br/TiO_2(rutile)$.

Promoter Example 14

$(Fe(NPh_2)_2Br)_n$ (0.2 g) was dissolved in 25 mL tetrahydrofuran. $TiO_2$ (rutile, 200° C. calcined) (4.0 g) was added to this solution, and the flask was swirled to form a slurry. The slurry was maintained at 60° C. overnight. The slurry was allowed to cool to room temperature, filtered, washed with tetrahydrofuran and dried under vacuum overnight.

Promoter Example 15

$(Fe(NPh_2)_2Br)_n$ (0.2 g) was dissolved in 25 mL of tetrahydrofuran. $TiO_2$ (rutile, 400° C. calcined) (4.3 g) was added to this solution, and a slurry obtained by swirling the flask. The slurry was maintained at 60° C. overnight. The slurry was allowed to cool to room temperature, filtered, washed with tetrahydrofuran, and dried under vacuum.

Promoter Example 16

$KFe(2,3-Me_2indolyl)_xBr_y$ (0.993 g) was combined with 5.1 g of $TiO_2$ (Alfa Aesar #40458, calcined to 400° C.) in 25 mL of cumene to form a slurry. The slurry was maintained at 100° C. overnight. The slurry was allowed to cool to room temperature, filtered, washed with cumene and dried.

Promoter Example 17

$KFe(2,3-Me_2indolyl)_xBr_y$ (0.9 g) was combined with 10 g of $TiO_2$ (rutile, calcined to 200° C.) in 25 mL of cumene to from a slurry. The slurry was maintained at 135° C. overnight. The slurry was allowed to cool to room temperature, filtered, washed with cumene and dried.

Promoter Example 18

$KFe(2,3-Me_2indolyl)_xBr_y$ (0.2 g) was combined with 5.1 g of $TiO_2$ (Alfa Aesar #40458, calcined to 800° C.) in 25 mL tetrahydrofuran to form a slurry. The slurry was maintained at 60° C. overnight. The slurry was allowed to cool to room temperature, filtered, washed with tetrahydrofuran and dried.

Oxidation Examples 19-28

The yield, conversion and selectivity of the alkyl benzene oxidation reactions with and without the $TiO_2$-supported promoters are provided in Table 3 below. In Table 2, in the "Selectivity" column, selectivity percentages followed by an "S" or an "A" refer to the selectivity for SBB hydroperoxide or acetophenone, respectively. The notation ND means the data were not determined.

TABLE 3

Oxidation with $TiO_2$-Supported Promoters

| Example | Alkyl Benzene Type | Qty. (g) | Promoter Type | Qty. (g) | Yield (%) | Conversion (%) | Selectivity (%) |
|---|---|---|---|---|---|---|---|
| 19 | CHB | 40 | None | 0 | 3.50 | ND | ND |
| 20 | CHB | 40 | P. Ex. 13 | 0.4 | 7.48 | 8.99 | 83.19 |
| 21 | CHB | 40 | P. Ex. 14 | 0.4 | 5.39 | 5.79 | 93.16 |
| 22 | CHB | 40 | P. Ex. 16 | 0.4 | 14.50 | 17.40 | 83.00 |
| 23 | CHB | 40 | P. Ex. 17 | 0.4 | 11.25 | 12.80 | 87.90 |
| 24 | SBB | 100 | None | 0 | ND | 0.90 | ND |
| 25 | SBB | 100 | P. Ex. 18 | 0.2 | ND | 6.49 | S 87.32 A 10.65 |
| 26 | SBB | 100 | P. Ex. 15 | 0.2 | ND | 7.60 | S 82.50 A 14.50 |
| 27 | SBB | 100 | P. Ex. 14 | 0.2 | ND | 6.10 | S 82.90 A 14.50 |

TABLE 3-continued

Oxidation with TiO$_2$-Supported Promoters

| Example | Alkyl Benzene Type | Qty. (g) | Promoter Type | Qty. (g) | Yield (%) | Conversion (%) | Selectivity (%) |
|---|---|---|---|---|---|---|---|
| 28 | SBB | 100 | P. Ex. 13 | 0.2 | ND | 5.20 | S 83.20 A 13.60 |

Examples 13-28 demonstrate the preparation and effect of promoters prepared on titanium oxide in the oxidation of alkyl benzenes. In the oxidation of sec-butyl benzene or cyclohexyl benzene, a promoter prepared on titanium oxide can have a hydroperoxide selectivity of greater than 80%, 85% or 90%. The conversion rate can be 15% or more.

All patents and other documents, including priority documents, cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains. Likewise, the term "comprising" is considered synonymous with the term "including" for purposes of Australian law.

What is claimed is:

1. A promoter for selective heterogeneous oxidation of arylalkyl hydrocarbons to form hydroperoxides, comprising the product of contacting:
    a solid support comprising a metal oxide surface; and
    an iron compound according to the formula $(Fe^{+n}(X^1R^1R^2)_x(X^2R^3)_yX^3_z)M^{n'}_p$;

wherein n is the valence of Fe and has a value of 2 or 3; $R^1$, $R^2$ and $R^3$ are the same or different and are independently selected from hydrogen and hydrocarbyls; $X^1$ is nitrogen or phosphorus; $X^2$ is oxygen or sulfur; $X^3$ is halogen; M is a cation of valence n' where n' is from 1 to 3; and p, x, y and z are numerical values wherein z is 0 or 1, p is 0, 1 or 2, at least one of x and y is equal to or greater than 1, and x+y+z=n+(n')(p) and $2 \leq (x+y+z) \leq 4$.

2. The promoter of claim 1, wherein the solid support comprises iron oxide.

3. The promoter of claim 1, wherein the solid support has magnetic susceptibility.

4. The promoter of claim 1, wherein the solid support comprises magnetite.

5. The promoter of claim 1, wherein the solid support comprises hematite.

6. The promoter of claim 1, wherein the solid support comprises titanium dioxide.

7. The promoter of claim 1, wherein $R^1$, $R^2$ and $R^3$ are selected from alkyl groups having from 1 to 30 carbon atoms and aryl and aralkyl groups having from 6 to 30 carbon atoms.

8. The promoter of claim 1, wherein M is selected from the group consisting of alkali metal cations, ammonium and phosphonium.

9. The promoter of claim 1 further comprising a slurry of the contact product on the support dispersed in a carrier liquid.

10. A method for oxidation of arylalkyl hydrocarbons to form hydroperoxides, comprising:
    contacting an arylalkyl hydrocarbon with oxygen in the presence of a promoter under catalytic oxidation conditions to form arylalkyl hydroperoxide;
    wherein the promoter comprises the product of contacting:
    a solid support comprising a metal oxide surface; and $(Fe^{+n}(X^1R^1R^2)_x(X^2R^3)_yX^3_z)M^{n'}_p$;

wherein n is the valence of Fe and has a value of 2 or 3; $R^1$, $R^2$ and $R^3$ are the same or different and are independently selected from hydrogen and hydrocarbyls; $X^1$ is nitrogen or phosphorus; $X^2$ is oxygen or sulfur; $X^3$ is halogen; M is a cation of valence n' where n' is from 1 to 3; and p, x, y and z are numerical values wherein z is 0 or 1, p is 0, 1 or 2, at least one of x and y is equal to or greater than 1, and x+y+z=n+(n')(p) and $2 \leq (x+y+z) \leq 4$.

11. The method of claim 10, wherein $R^1$, $R^2$ and $R^3$ are selected from alkyl groups having from 1 to 30 carbon atoms and aryl and aralkyl groups having from 6 to 30 carbon atoms.

12. The method of claim 10, wherein M is selected from the group consisting of alkali metal cations, ammonium and phosphonium.

13. The method of claim 10, further comprising recovering the promoter from the arylalkyl hydroperoxide.

14. The method of claim 13 wherein the recovery comprises filtration or centrifugation.

15. The method of claim 13 wherein the solid support has magnetic susceptibility and the recovery comprises magnetic separation.

16. The method of claim 13, further comprising recycling the recovered promoter to the contacting.

17. The method of claim 10, further comprising slurrying the promoter in a carrier liquid for the contacting.

18. The method of claim 10, wherein the arylalkyl hydrocarbon comprises cumene.

19. The method of claim 10, wherein the arylalkyl hydrocarbon comprises cyclohexyl benzene.

20. The method of claim 10, wherein the arylalkyl hydrocarbon comprises sec-butyl benzene.

21. The method of claim 10, wherein the solid support comprises iron oxide.

22. The method of claim 15, wherein the solid support comprises iron oxide.

23. The method of claim 10, wherein the solid support comprises magnetite.

24. The method of claim 15, wherein the solid support comprises magnetite.

25. The method of claim 10, wherein the solid support comprises hematite.

26. The method of claim 10, wherein the solid support comprises titanium dioxide.

27. The promoter of claim 1 wherein the metal from the metal oxide surface is selected from the group consisting of alkali metals, alkaline earth metals, rare earth metals, transition metals and main group metals.

28. The promoter of claim 1 wherein the solid support is a metal oxide selected from the group consisting of oxides of iron, titanium, manganese, cobalt, chromium, vanadium, molybdenum, copper, nickel, zinc, gallium, aluminum, indium, magnesium, and a combination thereof.

29. The method of claim 10 wherein the metal oxide surface is selected from the group consisting of iron oxides, titanium oxides, magnesium oxides, aluminum oxides and zirconium oxides.

30. The method of claim 10 wherein the metal oxide surface is selected from the group consisting of magnetite, hematite, titanium dioxide and combinations thereof.

31. The method of claim 10 wherein the solid support is a metal oxide selected from the group consisting of oxides of iron, titanium, manganese, cobalt, chromium, vanadium, molybdenum, copper, nickel, zinc, gallium, aluminum, indium, magnesium, and a combination thereof.

32. A promoter for selective heterogeneous oxidation of arylalkyl hydrocarbons to form hydroperoxides, comprising the product of contacting:

a solid support comprising a metal oxide surface selected from the group consisting of oxides of iron, titanium, manganese, cobalt, chromium, vanadium, molybdenum, copper, nickel, zinc, gallium, aluminum, indium, magnesium, and a combination thereof; and an iron compound according to the formula $$(Fe^{+n}(X^1R^1R^2)_x(X^2R^3)_y X^3_z)M^{n'}_p;$$

wherein n is the valence of Fe and has a value of 2 or 3; $R^1$, $R^2$ and $R^3$ are the same or different and are independently selected from hydrogen and hydrocarbyls; $X^1$ is nitrogen or phosphorus; $X^2$ is oxygen or sulfur; $X^3$ is halogen; p, x, y and z are numerical values wherein z is 0 or 1, p is 0, 1 or 2, at least one of x and y is equal to or greater than 1, and $x+y+z=n+(n)(p)$ and $2 \leq (x+y+z) \leq 4$; and M is a cation of valence n' where n' is from 1 to 3, where M is selected from the group consisting of alkali metal cations, ammonium and phosphonium.

33. A method for oxidation of arylalkyl hydrocarbons to form hydroperoxides, comprising:

contacting an arylalkyl hydrocarbon with oxygen in the presence of a promoter under catalytic oxidation conditions to form arylalkyl hydroperoxide;

wherein the promoter comprises the product of contacting:

a solid support comprising a metal oxide surface selected from the group consisting of oxides of iron, titanium, manganese, cobalt, chromium, vanadium, molybdenum, copper, nickel, zinc, gallium, aluminum, indium, magnesium, and a combination thereof; and $$(Fe^{+n}(X^1R^1R^2)_x(X^2R^3)_y X^3_z)M^{n'}_p;$$

wherein n is the valence of Fe and has a value of 2 or 3; $R^1$, $R^2$ and $R^3$ are the same or different and are independently selected from hydrogen and hydrocarbyls; $X^1$ is nitrogen or phosphorus; $X^2$ is oxygen or sulfur; $X^3$ is halogen; p, x, y and z are numerical values wherein z is 0 or 1, p is 0, 1 or 2, at least one of x and y is equal to or greater than 1, and $x+y+z=n+(n')(p)$ and $2 \leq (x+y+z) \leq 4$; and M is a cation of valence n' where n' is from 1 to 3, where M is selected from the group consisting of alkali metal cations, ammonium and phosphonium.

* * * * *